United States Patent
Park et al.

(10) Patent No.: US 12,059,364 B2
(45) Date of Patent: Aug. 13, 2024

(54) MOTION-MODE AND THUMB-POSITION-BASED MOTION CONTROL SYSTEM AND METHOD OF MYOELECTRIC HAND

(71) Applicant: KOREA LABOR WELFARE CORPORATION CO., LTD., Ulsan (KR)

(72) Inventors: Se Hoon Park, Bucheon-si (KR); Seung Gi Kim, Incheon (KR); Sung Yoon Jung, Incheon (KR); Suk Min Lee, Bucheon-si (KR)

(73) Assignee: KOREA LABOR WELFARE CORPORATION CO., LTD., Ulsan (KR)

( * ) Notice: Subject to any disclaimer, the term of this patent is extended or adjusted under 35 U.S.C. 154(b) by 224 days.

(21) Appl. No.: 17/386,955

(22) Filed: Jul. 28, 2021

(65) Prior Publication Data

US 2022/0039972 A1    Feb. 10, 2022

(30) Foreign Application Priority Data

Aug. 10, 2020  (KR) .................. 10-2020-0100014
Jun. 22, 2021  (KR) .................. 10-2021-0080838

(51) Int. Cl.
*A61F 2/72*  (2006.01)
*A61F 2/58*  (2006.01)

(52) U.S. Cl.
CPC ............. *A61F 2/72* (2013.01); *A61F 2/583* (2013.01); *A61F 2/586* (2013.01); *A61F 2002/587* (2013.01)

(58) Field of Classification Search
CPC .. A61F 2/583; A61F 2/586; A61F 2/68; A61F 2/72; A61F 2002/587
See application file for complete search history.

(56) References Cited

U.S. PATENT DOCUMENTS

| 2014/0128992 A1 | 5/2014 | Engeberg |
| 2015/0328019 A1 | 11/2015 | Park et al. |
| 2015/0351935 A1 | 12/2015 | Donati et al. |

FOREIGN PATENT DOCUMENTS

| KR | 10-2007-0080319 A |   | 8/2007 |
| KR | 20150106892 A | * | 2/2012 |

(Continued)

OTHER PUBLICATIONS

Translation of Donati. KR-20150106892A. (Year: 2012).*

(Continued)

*Primary Examiner* — Christie Bahena
(74) *Attorney, Agent, or Firm* — Maschoff Brennan

(57) ABSTRACT

Disclosed is a motion-mode- and thumb-position-based motion control system and method of a myoelectric hand, and more particularly a motion-mode- and thumb-position-based motion control system and method of a myoelectric hand that is capable of performing a hand motion indicating emotion or intention expression as well as a grasping motion for holding an object according to restrictive electromyography signals transmitted from two electromyography sensors provided at the myoelectric hand and that is capable of diversifying hand motions and grips depending on the position of a thumb that can be changed by a user, whereby a utilization range of the myoelectric hand is simply extended.

8 Claims, 4 Drawing Sheets

(56) References Cited

FOREIGN PATENT DOCUMENTS

| KR | 10-2012-0040431 A | 4/2012 | |
|---|---|---|---|
| KR | 10-2012-0133350 A | 12/2012 | |
| KR | 10-1465020 B | 11/2014 | |
| KR | 10-2015-0106892 A | 9/2015 | |
| KR | 10-1618706 B1 | 5/2016 | |
| KR | 10-1738098 B | 5/2017 | |
| KR | 10-2020-0114389 A | 10/2020 | |
| WO | WO-2008098072 A2 * | 8/2008 | ......... A61B 5/04888 |
| WO | 2012-071343 A1 | 5/2012 | |
| WO | WO-2012071343 A1 * | 5/2012 | ............. A61F 2/583 |
| WO | WO-2014197401 A2 * | 12/2014 | ............. A61F 2/583 |

OTHER PUBLICATIONS

KR Office Action in Application No. 10-2020-077794215 dated Nov. 9, 2020.
EP Search Report in Application No. 21189887.9 dated Jan. 19, 2022.

\* cited by examiner

MOTION-MODE AND THUMB-POSITION-BASED MOTION CONTROL SYSTEM AND METHOD OF MYOELECTRIC HAND This application claims the benefit of Korean Patent Application No. P2020-0100014, filed on Aug. 10, 2020, and Korean Patent Application No. P2021-0080838, filed on Jun. 22, 2021, which are hereby incorporated by reference as if fully set forth herein.

BACKGROUND OF THE INVENTION

Field of the Invention

The present invention relates to a motion-mode- and thumb-position-based motion control system and method of a myoelectric hand, and more particularly to a motion-mode- and thumb-position-based motion control system and method of a myoelectric hand that is capable of performing a hand motion indicating emotion or intention expression as well as a grasping motion for holding an object according to restrictive electromyography signals transmitted from two electromyography sensors provided at the myoelectric hand based on the position of the thumb by diversifying hand motions and grips, whereby a utilization range of the myoelectric hand is simply extended.

Discussion of the Related Art

Great inconvenience is caused in daily life without using various products and foods, such as computers, mobile phones, and bottled water, due to recent rapid economic development. For this reason, many handicapped people's demand for an assistance apparatus similar to a hand of a human being (a myoelectric hand), rather than conventional manual assistance apparatuses, has increased, and therefore research and development of various kinds of rehabilitation assistance apparatuses has been conducted.

In particular, a myoelectric hand for upper extremity amputees is a typical rehabilitation assistance apparatus that moves an artificial hand using an electromyography signal, which is an electric signal output from the muscle of an arm, to grasp an object, whereby handicapped people engage in independent social activities and daily living.

For the myoelectric hand, five-finger type products configured not only to stably hold various kinds of objects but also to express intentions or emotions, such as "thumbs-up" and "OK", using hand motions have increasingly come onto the market in recent years.

However, such a five-finger type myoelectric hand has not completely substituted for a conventional three-finger type myoelectric hand even up to now, i.e. 14 years after the five-finger type myoelectric hand was first developed in England in the year of 2006, and has many disadvantages in terms of durability, price, maintenance expenses, and convenience.

In particular, it is difficult to change hand motions in implementing various hand motions using the five-finger type myoelectric hand, and therefore many problems are caused in utilizing all advantages in that it is possible to implement two or more different hand motions, compared to conventional hand motions implemented to perform a simple grasping function.

That is, the conventional five-finger type myoelectric hand is capable of implementing various hand motions and grasping motions. In order to change motions, however, an additional control signal (button or gesture) other than a control signal constituted by only electromyography signals that a user can apply to the remaining muscle in order to perform a grasping motion is necessary, or an additional device, such as an application (APP) or dongle (wireless chip), is necessary. As a result, complexity in manipulation greatly increases.

Addition of devices or increase in complexity of manipulation abruptly deteriorates convenience in use. As a result, wide popularization of the five-finger type myoelectric hand is impeded.

PRIOR ART DOCUMENTS

Patent Documents (Patent Document 1) Korean Registered Patent No. 10-1618706

(Patent Document 2) Korean Patent Application Publication No. 10-2012-0040431

SUMMARY OF THE INVENTION

It is an object of the present invention to provide a motion-mode- and thumb-position-based motion control system and method of a myoelectric hand that is capable of performing a hand motion indicating emotion or intention expression as well as a grasping motion for holding an object according to restrictive electromyography signals transmitted from two electromyography sensors provided at the myoelectric hand and that is capable of diversifying hand motions and grips depending on the position of a thumb that can be changed by a user, whereby a utilization range of the myoelectric hand is simply extended.

In accordance with one aspect of the present invention, the above and other objects can be accomplished by the provision of a motion-mode- and thumb-position-based motion control system of a myoelectric hand, the motion-mode- and thumb-position-based motion control system including a motion mode switching unit configured to switch a motion that is performed by the myoelectric hand between a hand motion mode for intention and emotion expression and a grasping motion mode for holding an object to change a controller to be enabled, a thumb sensor configured to determine whether a thumb provided at the myoelectric hand is located at a horizontal position or a vertical position to implement a vertical thumb motion mode and a horizontal thumb motion mode, a hand motion controller configured to, when a main hand motion detailed motion mode or a subsidiary hand motion detailed motion mode matched with each of the horizontal thumb motion mode and the vertical thumb motion mode depending on the position of the thumb is selected in the hand motion mode enabled by the motion mode switching unit, receive an electromyography signal transmitted from at least one of first and second electromyography sensors attached to a human body, to enable a control signal for driving the myoelectric hand in order to implement a hand motion matched with the main hand motion detailed motion mode or the subsidiary hand motion detailed motion mode, and to transmit the control signal to a driving unit of the myoelectric hand, and a grasping motion controller configured to, when a main grasping motion detailed motion mode or a subsidiary grasping motion detailed motion mode matched with each of the horizontal thumb motion mode and the vertical thumb motion mode depending on the position of the thumb is selected in the grasping motion mode enabled by the motion mode switching unit, receive an electromyography signal transmitted from at least one of the first and second electromyography sensors, to enable a control signal for driving the myoelectric hand in order to implement a grasping motion matched with the main grasping motion detailed motion mode or the subsidiary grasping motion detailed motion mode, and to transmit the control signal to the driving unit of the myoelectric hand, wherein the motion mode switching unit switches between the hand motion mode and the grasping motion mode through a plurality of combined signals applied from the first and second electromyography sensors to change the controller to be enabled.

The plurality of combined signals may include a simultaneous enabling signal, in which values of HIGH are applied from both the first and second electromyography sensors, and a double open signal, in which a value of LOW is applied from the first electromyography sensor and a value of HIGH is applied twice from the second electromyography sensor for a predetermined time.

The hand motion controller may include a hand motion setting unit configured to store a control signal matched with a driving signal for manipulating the driving unit of the myoelectric hand so as to unbend or bend fingers according to an enabling signal constituted by the electromyography signal transmitted from the first or second electromyography sensor in each detail motion mode of the hand motion mode, a thumb sensing unit configured to select and enable a horizontal thumb hand motion mode or a vertical thumb hand motion mode matched with position information of the thumb transmitted from the thumb sensor in the state in which the hand motion mode is enabled, and a hand motion execution unit configured to derive a control signal matched with a preset main hand motion detail motion mode or a preset subsidiary hand motion detail motion mode according to the enabling signal transmitted from the first or second electromyography sensor in the state in which the hand motion mode selected by the thumb sensing unit is enabled and to transmit the control signal to the driving unit.

The hand motion setting unit may be configured to generate and store a first enabling signal (close) in which a value of HIGH is input from the first electromyography sensor and a value of LOW is input from the second electromyography sensor, a second enabling signal (open) in which a value of LOW is input from the first electromyography sensor and a value of HIGH is input from the second electromyography sensor, and a control signal matched with each enabling signal such that switching between a horizontal thumb main hand motion mode and a horizontal thumb subsidiary hand motion mode is performed or at least one subsequent motion mode connected to the horizontal thumb main hand motion mode and at least one subsequent motion mode connected to the horizontal thumb subsidiary hand motion mode are performed depending on the number of generation times of each signal in the horizontal thumb hand motion mode in which the thumb is located at a horizontal position.

In addition, the hand motion setting unit may be configured to set switching between the horizontal thumb main hand motion mode and the horizontal thumb subsidiary hand motion mode whenever the second enabling signal (open) is input in the horizontal thumb hand motion mode, to set a horizontal thumb first main hand motion detail motion mode so as to perform a hand motion indicating "scissors" of rock paper scissors when the first enabling signal (close) is input in the horizontal thumb main hand motion mode, to set a horizontal thumb second main hand motion detail motion mode so as to perform a hand motion indicating "rock" of the rock paper scissors when the first enabling signal (close) is input again in the horizontal thumb first main hand motion detail motion mode, to set returning to the horizontal thumb hand motion mode when the second enabling signal (open) is input in the horizontal thumb second main hand motion detail motion mode, to set a vertical thumb first subsidiary hand motion detail motion mode so as to perform a hand motion indicating "thumbs-up" when the first enabling signal (close) is input in the horizontal thumb subsidiary hand motion mode, and to set returning to the horizontal thumb hand motion mode when the second enabling signal (open) is input in the vertical thumb first subsidiary hand motion detail motion mode.

In addition, the hand motion setting unit may be configured to generate and store a first enabling signal (close) in which a value of HIGH is input from the first electromyography sensor and a value of LOW is input from the second electromyography sensor, a second enabling signal (open) in which a value of LOW is input from the first electromyography sensor and a value of HIGH is input from the second electromyography sensor, and a control signal matched with each enabling signal such that switching between a vertical thumb main hand motion mode and a vertical thumb subsidiary hand motion mode is performed or at least one first main hand motion mode connected to the vertical thumb main hand motion mode and at least one second subsidiary hand motion mode connected to the vertical thumb subsidiary hand motion mode are performed depending on the number of generation times of each signal in the vertical thumb hand motion mode in which the thumb is located at a vertical position.

In addition, the hand motion setting unit may be configured to set switching between the vertical thumb main hand motion mode and the vertical thumb subsidiary hand motion mode whenever the second enabling signal (open) is input in the vertical thumb hand motion mode, to set a vertical thumb first main hand motion detail motion mode so as to perform an "indexing" hand motion indicating an object or choosing a target when the first enabling signal (close) is input in the vertical thumb main hand motion mode, to set returning to the vertical thumb hand motion mode when the second enabling signal (open) is input in the vertical thumb first main hand motion detail motion mode, to set a vertical thumb first subsidiary hand motion detail motion mode so as to perform an "OK" hand motion when the first enabling signal (close) is input in the vertical thumb subsidiary hand motion mode, and to set returning to the vertical thumb hand motion mode when the second enabling signal (open) is input in the vertical thumb first subsidiary hand motion detail motion mode.

The grasping motion controller may include a grasping motion setting unit configured to store a control signal matched with a driving signal for manipulating the driving unit of the myoelectric hand so as to grasp an object while unbending or bending fingers according to an enabling signal constituted by the electromyography signal transmitted from the first or second electromyography sensor in each detail motion mode of the grasping motion mode, a thumb sensing unit configured to select and enable a horizontal thumb grasping motion mode or a vertical thumb grasping motion mode matched with position information of the thumb transmitted from the thumb sensor in the state in which the grasping motion mode is enabled, and a grasping motion execution unit configured to derive a control signal matched with a preset main grasping motion detail motion mode or a preset subsidiary grasping motion detail motion mode according to an enabling signal transmitted from the first or second electromyography sensor in the state in which the grasping motion mode selected by the thumb sensing unit is enabled and to transmit the control signal to the driving unit.

The grasping motion setting unit may be configured to generate and store a first enabling signal (close) in which a value of HIGH is input from the first electromyography sensor and a value of LOW is input from the second electromyography sensor, a second enabling signal (open) in which a value of LOW is input from the first electromyography sensor and a value of HIGH is input from the second electromyography sensor, and a control signal matched with each enabling signal such that switching between a horizontal thumb main grasping motion mode and a horizontal thumb subsidiary grasping motion mode is performed or at least one subsequent motion mode connected to the horizontal thumb main grasping motion mode and at least one subsequent motion mode connected to the horizontal thumb subsidiary grasping motion mode are performed depending on the number of generation times of each signal in the horizontal thumb grasping motion mode in which the thumb is located at a horizontal position.

In addition, the grasping motion setting unit may be configured to set switching between the horizontal thumb main grasping motion mode and the horizontal thumb subsidiary grasping motion mode whenever the second enabling signal (open) is input in the horizontal thumb grasping motion mode, to set a horizontal thumb first main grasping motion detail motion mode so as to perform a "cylinder grip" grasping motion when the first enabling signal (close) is input in the horizontal thumb main grasping motion mode, to set returning to the horizontal thumb grasping motion mode when the second enabling signal (open) is input in the horizontal thumb first main grasping motion detail motion mode, to set a vertical thumb first subsidiary grasping motion detail motion mode so as to perform a "lateral grip" grasping motion when the first enabling signal (close) is input in the horizontal thumb subsidiary grasping motion mode, and to set returning to the horizontal thumb grasping motion mode when the second enabling signal (open) is input in the vertical thumb first subsidiary grasping motion detail motion mode.

In addition, the grasping motion setting unit may be configured to generate and store a first enabling signal (close) in which a value of HIGH is input from the first electromyography sensor and a value of LOW is input from the second electromyography sensor, a second enabling signal (open) in which a value of LOW is input from the first electromyography sensor and a value of HIGH is input from the second electromyography sensor, and a control signal matched with each enabling signal such that switching between a vertical thumb main grasping motion mode and a vertical thumb subsidiary grasping motion mode is performed or at least one subsequent motion mode connected to the vertical thumb main grasping motion mode and at least one subsequent motion mode connected to the vertical thumb subsidiary grasping motion mode are performed depending on the number of generation times of each signal in the vertical thumb grasping motion mode in which the thumb is located at a vertical position.

In addition, the grasping motion setting unit may be configured to set switching between the vertical thumb main grasping motion mode and the vertical thumb subsidiary grasping motion mode whenever the second enabling signal (open) is input in the vertical thumb grasping motion mode, to set a vertical thumb first main grasping motion detail motion mode so as to perform a "power grip" grasping motion when the first enabling signal (close) is input in the vertical thumb main grasping motion mode, to set returning to the vertical thumb grasping motion mode when the second enabling signal (open) is input in the vertical thumb first main grasping motion detail motion mode, to set a vertical thumb first subsidiary grasping motion detail motion mode so as to perform a "tip (precision) grip" grasping motion when the first enabling signal (close) is input in the vertical thumb subsidiary grasping motion mode, and to set returning to the vertical thumb grasping motion mode when the second enabling signal (open) is input in the vertical thumb first subsidiary grasping motion detail motion mode.

In accordance with another aspect of the present invention, there is provided a control method using the motion-mode- and thumb-position-based motion control system, the control method including a motion-mode- and thumb-position-based motion setting step of classifying motion modes to be implemented by the myoelectric hand into a hand motion mode and a grasping motion mode and setting and storing, for each of horizontal thumb and vertical thumb motion modes, a control signal for forming the shape of fingers or a grip to be implemented in each motion mode, a motion mode switching step of, when signals are input from two electromyography sensors provided at the myoelectric hand, switching a motion mode to be enabled between the hand motion mode and the grasping motion mode, a thumb position sensing step of acquiring the position of a thumb manipulated by a user based on position information transmitted from a thumb sensor to determine whether the motion mode is a vertical thumb motion mode or a horizontal thumb motion mode, a detail motion mode selection step of determining whether the position of the thumb is a horizontal position or a vertical position and enabling a main motion detail motion mode and a subsidiary motion detail motion mode set in each motion mode, a control signal enabling step of deriving a control signal for performing a hand motion or a grasping motion set in each of the main motion detail motion mode and the subsidiary motion detail motion mode according to electromyography signals transmitted from the two electromyography sensors, and a motion implementing step of, upon receiving the enabled control signal, the myoelectric hand performing the set hand motion or grasping motion while bending or unbending joints of the fingers.

The motion-mode- and thumb-position-based motion setting step may include a motion mode setting process of setting motions to be implemented by the myoelectric hand so as to be classified into a hand motion mode for showing shapes of fingers used for emotion expression or intention expression and a grasping motion mode for forming various grips to hold an object, a thumb position motion mode setting process of storing the shapes of the fingers or the grips to be implemented in each motion mode in a state of being matched with the vertical position and the horizontal position based on position information of the thumb to set a horizontal thumb motion mode and a vertical thumb motion mode, a detail motion mode setting process of setting a main motion detail motion mode and a subsidiary motion detail motion mode matched with each of the vertical thumb motion mode and the horizontal thumb motion mode in order to implement the shapes of the fingers and the grips in the thumb position motion mode, and a control signal matching process of storing a control signal for driving the myoelectric hand such that joints of the fingers of the myoelectric hand are bent or unbent in order to implement the shapes of the fingers and the grips in a state of being matched with each shape of fingers and each grip.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Figure 1:
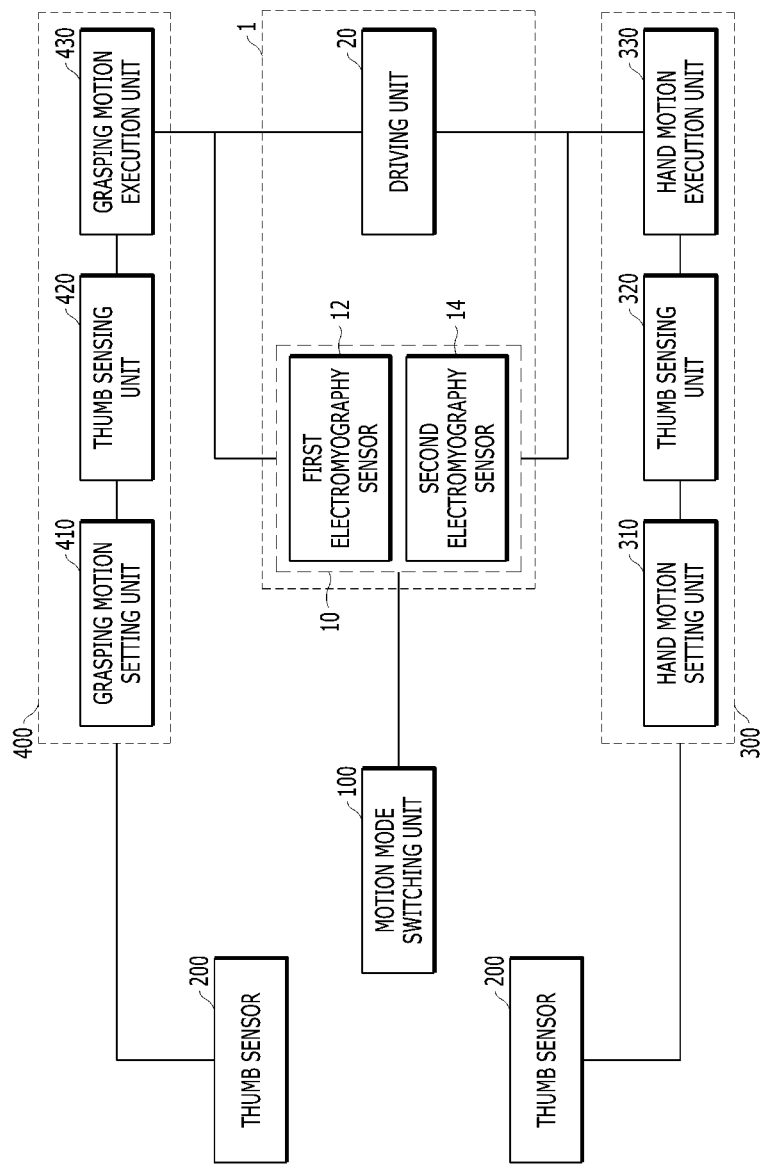
FIG. 1 is a block diagram of a motion-mode- and thumb-position-based motion control system of a myoelectric hand according to the present invention.

Hereinafter, some embodiments of the present invention will be described with reference to the accompanying drawings. In the drawings, the same or similar elements are denoted by the same reference numerals even though they are depicted in different drawings. In the following description, a detailed description of known functions and configurations incorporated herein will be omitted when it may make the subject matter of the disclosure rather unclear.

Also, in describing the components of embodiments of the present invention, terms such as "first," "second," "A," "B," "(a)," and "(b)" may be used. These terms are used only for the purpose of distinguishing one constituent from another, and the terms do not limit the nature, order or sequence of the components. When one component is said to be "connected," "coupled," or "linked" to another, this may mean not only that the one component is directly connected, coupled, or linked to the other one but also that the one component is "connected," "coupled," or "linked" to the other one via yet another component interposed therebetween.

Figure 2:
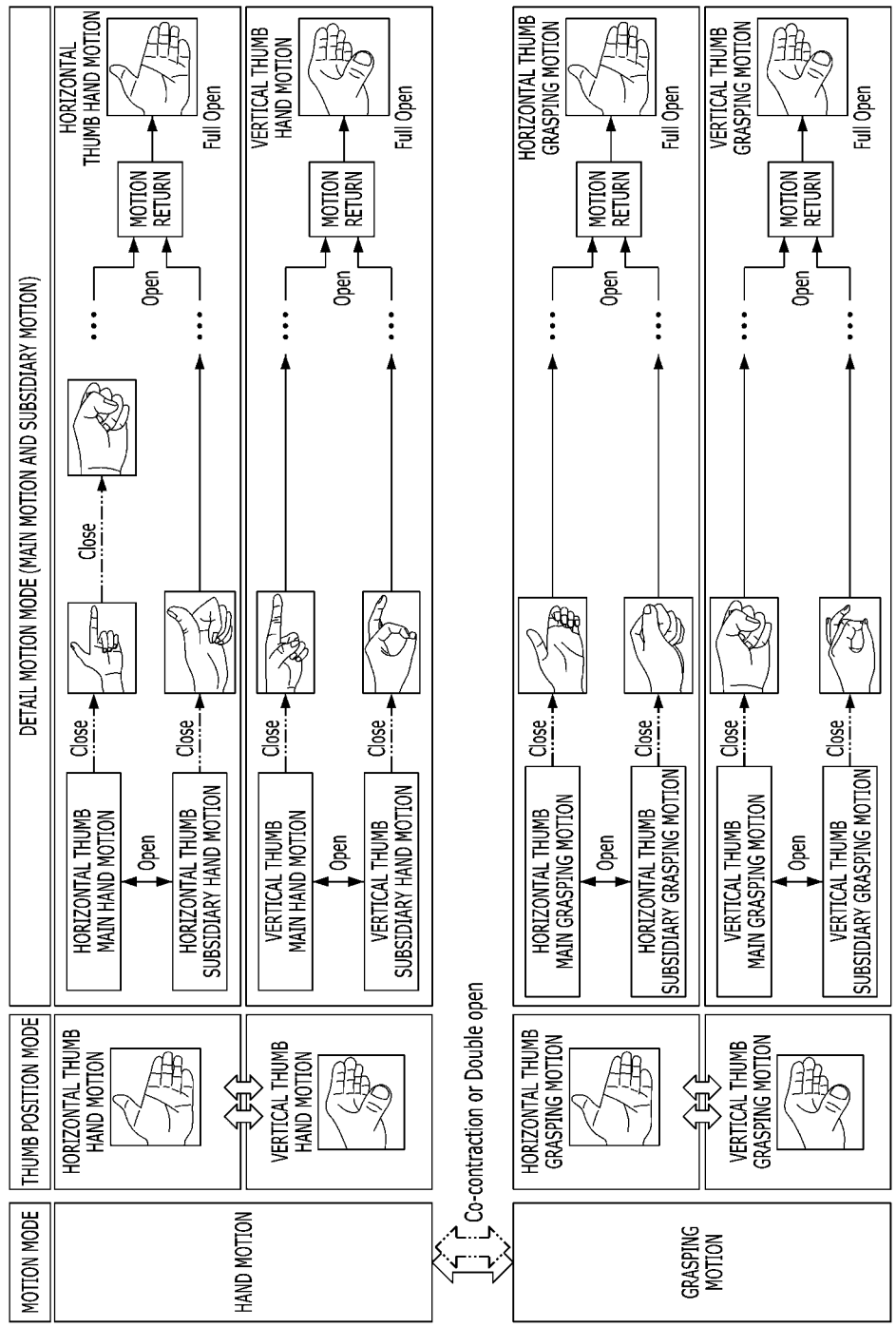
FIG. 2 is a view showing main/subsidiary hand motions and main/subsidiary grasping motions based on the position of a thumb and the state of an electromyographic signal in accordance with the present invention.

FIG. 1 is a block diagram of a motion-mode- and thumb-position-based motion control system of a myoelectric hand according to the present invention, and FIG. 2 is a view showing main/subsidiary hand motions and main/subsidiary grasping motions based on the position of a thumb and the state of an electromyographic signal in accordance with the present invention.

Referring to FIGS. 1 and 2, the motion-mode- and thumb-position-based motion control system of the myoelectric hand according to the present invention includes a motion mode switching unit 100, a thumb sensor 200, a hand motion controller 300, and a grasping motion controller 400, and is configured to perform both a hand motion and a grasping motion using the same electromyographic signals.

The motion mode switching unit 100 switches a motion that is performed by the myoelectric hand between a hand motion mode for intention and emotion expression and a grasping motion mode for holding an object to change a motion controller to be enabled when electromyography signals are applied together from two electromyography sensors 10 provided at the myoelectric hand or when HIGH signals are successively input.

When a thumb provided at the myoelectric hand is manually rotated by a user or is automatically rotated according to the above two signals, the thumb sensor 200 determines whether the rotated thumb is located at a horizontal position or a vertical position to classify a thumb motion mode into a vertical thumb motion mode and a horizontal thumb motion mode.

When a main hand motion detail motion mode and a subsidiary hand motion detail motion mode matched with each of a horizontal thumb hand motion mode and a vertical thumb hand motion mode depending on the position of the thumb are selected in the hand motion mode enabled by the motion mode switching unit 100, the hand motion controller 300 receives an electromyography signal transmitted from any one of the electromyography sensors, enables a control signal for driving the myoelectric hand in order to implement a hand motion matched with each detail mode, and transmits the control signal to a driving unit of the myoelectric hand.

When a main grasping motion detail motion mode and a subsidiary grasping motion detail motion mode matched with each of a horizontal thumb grasping motion mode and a vertical thumb grasping motion mode depending on the position of the thumb are selected in the grasping motion mode enabled by the motion mode switching unit 100, the grasping motion controller 400 receives an electromyography signal transmitted from any one of the electromyography sensors, enables a control signal for driving the myoelectric hand in order to implement a grasping motion matched with each detail motion mode, and transmits the control signal to the driving unit of the myoelectric hand.

That is, in the present invention, in not only grasping an object but also performing a simple hand motion indicating intention expression or emotion expression of the user using a five-finger type articulated myoelectric hand 1, it is possible to implement both motions using only electromyography signals generated by the two electromyography sensors conventionally used to control a grasping motion without provision of an additional device, such as an application (APP) or dongle capable of generating a new driving signal, unlike the conventional art.

Consequently, signals applied by the user who wears the myoelectric hand 1 in order to implement the hand motion for intention expression or emotion expression in the present invention are merely electromyography signals that can be acquired by the two electromyography sensors conventionally attached to the human body in order to perform an object grasping motion, whereby it is possible to more conveniently express a simple hand motion without learning a new complicated manipulation method.

In order to implement both the grasping motion and the hand motion using restrictive electromyography signals transmitted from the two electromyography sensors, the myoelectric hand 1 includes two electromyography sensors 10 attached to the skin of the user to acquire electromyography signals and a driving unit 20 driven according to the electromyography signals acquired by the electromyography sensors 10 to bend or unbend joints of fingers.

Combinations of electromyography signals generated by the two electromyography sensors 12 and 14 may include the case in which both the two electromyography sensors sense enabling signals and the case in which only one of the two electromyography sensors senses an enabling signal. In the present invention, it is possible to grasp an object and to perform a simple hand motion using only such three signals. In the case in which a control signal for automatically moving the thumb to the vertical position or the horizontal position is necessary or in the case in which an additional signal capable of replacing a simultaneous enabling signal is necessary, successive HIGH signals may be additionally used.

That is, as shown in Table 1 below, signals generated by the two electromyography sensors 12 and 14 attached to the human body constitute a simultaneous enabling signal (shown as a co-contraction signal in FIG. 2), in which both a first electromyography signal transmitted from the first electromyography sensor 12 and a second electromyography signal transmitted from the second electromyography sensor 14 have values of HIGH, a first enabling signal (shown as a close signal in FIG. 2), in which the first electromyography signal has a value of HIGH and the second electromyography signal has a value of LOW, and a second enabling signal (shown as an open signal in FIG. 2), in which the first electromyography signal has a value of LOW and the second electromyography signal has a value of HIGH. In the case in which the thumb is automatically moved and an additional signal is necessary, successive HIGH signals (double open) input within a set time may be additionally used. At this time, when a value of HIGH is applied from each electromyography sensor, this refers to an enabling signal indicating that the electromyography sensor is enabled.

TABLE 1

|  | Simultaneous enabling signal (co-contraction) | First enabling signal (close) | Second enabling signal | Double open (open) |
|---|---|---|---|---|
| First electromyography signal | HIGH | HIGH | LOW | LOW |
| Second electromyography signal | HIGH | LOW | HIGH | HIGH + HIGH |

Among the four signals, the double open signal and the simultaneous enabling signal (co-contraction), which are switching signals capable of changing a motion mode between the hand motion mode and the grasping motion mode, are configured to be used by the motion mode switching unit 100 or to be used for switching between a vertical position motion mode and a horizontal position motion mode when the thumb is automatically moved, and the first enabling signal (close) and the second enabling signal, which are control signals for performing the hand motion and the grasping motion preset depending on the position of the thumb in the hand motion mode and the grasping motion mode, are configured to be used by the hand motion controller 300 and the grasping motion controller 400, respectively.

Consequently, the motion mode switching unit 100, which switches a motion to be performed using the myoelectric hand between the hand motion mode and the grasping motion mode, switches between the hand motion mode and the grasping motion mode through a plurality of combined signals applied from the first electromyography sensor 12 and the second electromyography sensor 14 to change the controller to be enabled. That is, the motion mode switching unit 100 is configured to switch the controller between the hand motion controller 300 and the grasping motion controller 400 whenever the simultaneous enabling signal, in which values of HIGH are applied from the two electromyography sensors, is input or whenever the double open signal is enabled as needed.

That is, when values of HIGH are input from both the first electromyography sensor 12 and the second electromyography sensor 14 in the current hand motion mode (shown as a co-contraction signal in FIG. 2) or when the double open signal is input, the motion mode switching unit 100 disables the hand motion mode, which is currently enabled, and enables the grasping motion mode, whereby the grasping motion controller 400 applies a control signal for bending or unbending fingers to the driving unit 20 of the myoelectric hand.

In addition, when values of HIGH are input from both the first electromyography sensor 12 and the second electromyography sensor 14 in the grasping motion mode (shown as a co-contraction signal in FIG. 2) or when the double open signal is input, the motion mode switching unit 100 disables the grasping motion mode, which is currently enabled, and enables the hand motion mode, whereby the hand motion controller 300 applies a control signal for bending or unbending fingers to the driving unit of the myoelectric hand.

Since a controller that is enabled and outputs a control signal is changed by the motion mode switching unit 100, as described above, it is possible to perform the grasping motion and the hand motion using the same electromyography signal transmitted from any one electromyography sensor without addition of a separate additional device.

In addition, the thumb sensor 200, which determines whether the thumb provided at the myoelectric hand is located at the horizontal position or the vertical position and thus determines whether the motion mode is the vertical thumb motion mode or the horizontal thumb motion mode, is configured to sense the position of the thumb in order to set the main hand motion detail motion mode and the subsidiary hand motion detail motion mode that can be implemented in the hand motion mode and the main grasping motion detail motion mode and the subsidiary grasping motion detail motion mode that can be implemented in the grasping motion mode.

At this time, the position of the thumb may be changed by the user manually rotating the thumb, or may be automatically changed using the double open signal (or a combination of the co-contraction signal and the two signals). In this embodiment, the case in which the rotated thumb is located so as to be parallel to other fingers (a lateral direction) is referred to as a horizontal position, and the case in which the rotated thumb is located so as to be perpendicular to other fingers (a forward direction) is referred to as a vertical position. However, the present invention is not limited thereto. The position of the thumb may be variously set.

The hand motion controller 300 includes a hand motion setting unit 310, a thumb sensing unit 320, and a hand motion execution unit 330.

The hand motion setting unit 310 stores a control signal matched with a driving signal for manipulating the driving unit of the myoelectric hand so as to unbend or bend fingers according to an enabling signal constituted by an electromyography signal transmitted from the first or second electromyography sensor in each detail motion mode of the hand motion mode.

The thumb sensing unit 320 selects and enables the horizontal thumb hand motion mode and the vertical thumb hand motion mode matched with position information of the thumb transmitted from the thumb sensor in the state in which the hand motion mode is enabled.

The hand motion execution unit 330 derives a control signal matched with a first main hand motion detail motion mode and a first subsidiary hand motion detail motion mode, which are preset, according to an enabling signal transmitted from the first or second electromyography sensor in the state in which the detail motion mode selected by the thumb sensing unit is enabled, and transmits the control signal to the driving unit.

At this time, the hand motion setting unit 310 is configured to store a driving signal for manipulating the driving unit of the myoelectric hand so as to unbend or bend the fingers in order to perform a hand motion to be shown in each detail motion mode of the hand motion mode in a state of being matched with an enabling signal transmitted from the first or second electromyography sensor.

To this end, the vertical thumb hand motion mode, in which the thumb is located at the vertical position, is classified into a vertical thumb main hand motion detail motion mode and a vertical thumb subsidiary hand motion detail motion mode, and the hand motion setting unit 310 is configured to generate and store a control signal in which each enabling signal is matched with a driving signal for bending or unbending the joints of the fingers in order to show a vertical thumb first main hand motion to be performed in a first enabling signal state and a vertical thumb first subsidiary hand motion detail motion mode expressing the state in which a value of HIGH is input from the second electromyography sensor for a sufficient time (0.5 to 1 second) and a value of LOW is input from the first electromyography sensor in a vertical thumb first main hand motion detail motion mode. In addition, extension from the vertical thumb first main hand motion detail motion mode or the vertical thumb first subsidiary hand motion detail motion mode to a vertical thumb second main hand motion detail motion mode or a vertical thumb second subsidiary hand motion detail motion mode expressing a first enabling signal state is possible, as needed.

That is, the hand motion setting unit 310 is configured to generate and store a first enabling signal (close) in which a value of HIGH is input from the first electromyography sensor and a value of LOW is input from the second electromyography sensor, a second enabling signal (open) in which a value of LOW is input from the first electromyography sensor and a value of HIGH is input from the second electromyography sensor, and a control signal matched with each enabling signal such that switching between the vertical thumb main hand motion mode and the vertical thumb subsidiary hand motion mode is performed or at least one first main hand motion mode connected to the vertical thumb main hand motion mode and at least one second subsidiary hand motion mode connected to the vertical thumb subsidiary hand motion mode are performed depending on the number of generation times of each signal in the vertical thumb hand motion mode in which the thumb is located at the vertical position.

In addition, the horizontal thumb hand motion mode, in which the thumb is located at the horizontal position, is classified into a horizontal thumb main hand motion detail motion mode and a horizontal thumb subsidiary hand motion detail motion mode, and the hand motion setting unit 310 is configured to generate and store a control signal in which each enabling signal is matched with a driving signal for bending or unbending the joints of the fingers in order to show a horizontal thumb first main hand motion detail motion mode to be performed in the first enabling signal state and a horizontal thumb first subsidiary hand motion detail motion mode expressing the state in which a value of HIGH is input from the second electromyography sensor for a sufficient time and a value of LOW is input from the first electromyography sensor in the horizontal thumb first main hand motion detail motion mode. In addition, extension from the horizontal thumb first main hand motion detail motion mode or the horizontal thumb first subsidiary hand motion detail motion mode to a horizontal thumb second main hand motion detail motion mode or a horizontal thumb second subsidiary hand motion detail motion mode expressing a first enabling signal state is possible, as needed.

That is, the hand motion setting unit 310 is configured to generate and store a first enabling signal (close) in which a value of HIGH is input from the first electromyography sensor and a value of LOW is input from the second electromyography sensor, a second enabling signal (open) in which a value of LOW is input from the first electromyography sensor and a value of HIGH is input from the second electromyography sensor, and a control signal matched with each enabling signal such that switching between the horizontal thumb main hand motion mode and the horizontal thumb subsidiary hand motion mode is performed or at least one subsequent motion mode connected to the horizontal thumb main hand motion mode and at least one subsequent motion mode connected to the horizontal thumb subsidiary hand motion mode are performed depending on the number of generation times of each signal in the horizontal thumb hand motion mode in which the thumb is located at the horizontal position.

In this embodiment, as shown in FIG. 2, in the vertical thumb main hand motion mode in which the thumb is located at the vertical position, an "indexing" hand motion, which is a vertical thumb first main hand motion, is set in the first enabling signal state (shown as a close signal in FIG. 2), switching from a vertical thumb first main hand motion detail mode to a vertical thumb first subsidiary hand motion detail mode indicating the state in which a value of HIGH is input from the second electromyography sensor for a sufficient time and a value of LOW is input from the first electromyography sensor (an open signal), and an "OK" hand motion, which is the vertical thumb first subsidiary hand motion detail mode, is set.

Also, in the horizontal thumb hand motion mode in which the thumb is located at the horizontal position, a hand motion indicating "scissors" of rock paper scissors, which is the horizontal thumb first main hand motion mode, is set in the first enabling signal state (shown as a close signal in FIG. 2), switching from a horizontal thumb first main hand motion detail mode to a horizontal thumb first subsidiary hand motion detail mode indicating the state in which a value of HIGH is input from the second electromyography sensor for a sufficient time and a value of LOW is input from the first electromyography sensor (an open signal), and a hand motion indicating "thumbs-up", which is the horizontal thumb first subsidiary hand motion detail mode, is set.

The thumb sensing unit 320 is configured to enable a detail motion mode matched with the horizontal thumb motion mode or the vertical thumb motion mode based on the position information of the thumb transmitted from the thumb sensor 200 in the state in which the hand motion mode is enabled after setting of a hand motion to be performed is completed using the fingers of the myoelectric hand.

At this time, of course, the detailed motion mode of the hand motion mode that is enabled is changed whenever the user manually or automatically rotates the thumb to change the position of the thumb from the horizontal position to the vertical position or from the vertical position to the horizontal position.

In addition, the hand motion execution unit 330 is configured to derive a control signal matched with an enabling signal transmitted from the first or second electromyography sensor in the state in which a thumb position mode selected based on the position of the thumb is enabled and to transmit the control signal to the driving unit of the myoelectric hand.

As shown in FIG. 2, therefore, when the first enabling signal (close signal), in which a value of HIGH is input from only the first electromyography sensor, is applied in the vertical thumb motion mode in which the thumb is located at the vertical position, the hand motion execution unit 330 enables a control signal constituted by driving signals for moving the joints of the fingers so as to show the "indexing" gesture, which is the vertical thumb first main hand motion detail motion mode, matched with the first enabling signal, and transmits the control signal to the driving unit of the myoelectric hand. The fingers of the myoelectric hand are driven according to the control signal transmitted under control of the hand motion execution unit, whereby it is possible to show the "indexing" gesture, as shown in FIG. 2.

Afterwards, when a signal (open signal in FIG. 2) opposite the first enabling signal (close signal) is input from the first or second electromyography sensor, the fingers of the myoelectric hand are restored to the state before the hand motion is performed. At this time, when an opposite signal (open signal in FIG. 2) is input for a sufficient time, a new detail motion mode is ready through detail motion mode switching. That is, a main motion detail motion mode is switched to a subsidiary motion detail motion mode, and the subsidiary motion detail motion mode is switched to the main motion detail motion mode.

Also, in order to show the vertical thumb first subsidiary hand motion detail motion mode expressing the state in which a value of HIGH is input from the second electromyography sensor for a sufficient time and a value of LOW is input from the first electromyography sensor in the vertical thumb first main hand motion detail motion mode, the motion execution unit enables and transmits a control signal for moving the joints of the fingers so as to show the "OK" gesture, which is the vertical thumb first subsidiary hand motion. In the vertical thumb first subsidiary hand motion detail motion mode, therefore, the fingers of the myoelectric hand are driven when the first enabling signal (close signal) is generated, whereby it is possible to show the "OK" gesture indicating an object or a direction, as shown in FIG. 2.

Afterwards, when a signal (open signal in FIG. 2) opposite the first enabling signal (close signal) is input from the first or second electromyography sensor, the fingers of the myoelectric hand are restored to the state before the hand motion is performed. At this time, when an opposite signal (open signal in FIG. 2) is input for a sufficient time, a new detail motion mode is ready through detail motion mode switching. That is, the main motion detail motion mode is switched to the subsidiary motion detail motion mode, and the subsidiary motion detail motion mode is switched to the main motion detail motion mode.

In addition, when the first enabling signal (close signal), in which a value of HIGH is input from only the first electromyography sensor, is applied in the horizontal thumb mode in which the thumb is located at the horizontal position, as shown in FIG. 2, the hand motion execution unit enables a control signal for moving the joints of the fingers so as to show the "scissors" gesture of rock paper scissors, which is the horizontal thumb first main hand motion, matched with the first enabling signal and to transmit the control signal to the driving unit of the myoelectric hand. As a result, the fingers of the myoelectric hand are driven, whereby it is possible to show the "scissors" gesture indicating an object or a direction, as shown in FIG. 2.

Afterwards, when a signal (open signal in FIG. 2) opposite the first enabling signal (close signal) is input from the first or second electromyography sensor, the fingers of the myoelectric hand are restored to the state before the hand motion is performed. At this time, when an opposite signal (open signal in FIG. 2) is input for a sufficient time, a new detail motion mode is ready through detail motion mode switching. That is, the main motion detail motion mode is switched to the subsidiary motion detail motion mode, and the subsidiary motion detail motion mode is switched to the main motion detail motion mode.

Also, in order to show the horizontal thumb first subsidiary hand motion detail motion mode expressing the state in which a value of HIGH is input from the second electromyography sensor for a sufficient time and a value of LOW is input from the first electromyography sensor in the horizontal thumb first main hand motion detail motion mode, the motion execution unit enables and transmits a control signal for moving the joints of the fingers so as to show the "thumbs-up" gesture, which is the horizontal thumb first subsidiary hand motion. In the horizontal thumb second subsidiary hand motion detail motion mode, therefore, the fingers of the myoelectric hand are driven when the first enabling signal (close signal) is generated, whereby it is possible to show the "thumbs-up" gesture, as shown in FIG. 2.

Afterwards, when a signal (open signal in FIG. 2) opposite the first enabling signal (close signal) is input from the first or second electromyography sensor, the fingers of the myoelectric hand are restored to the state before the hand motion is performed. At this time, when an opposite signal (open signal in FIG. 2) is input for a sufficient time, a new detail motion mode is ready through detail motion mode switching. That is, the main motion detail motion mode is switched to the subsidiary motion detail motion mode, and the subsidiary motion detail motion mode is switched to the main motion detail motion mode. In addition, the type of the hand motion set in each detail motion mode is not limited thereto, and various settings are possible depending on the hand motion forms that the user mainly uses.

The grasping motion controller 400 includes a grasping motion setting unit 410, a thumb sensing unit 420, and a grasping motion execution unit 430.

The grasping motion setting unit 410 stores a control signal matched with a driving signal for manipulating the driving unit of the myoelectric hand so as to grasp an object while unbending or bending fingers according to an enabling signal constituted by an electromyography signal transmitted from the first or second electromyography sensor in each detail motion mode of the grasping motion mode.

The thumb sensing unit 420 selects and enables the horizontal thumb grasping motion mode and the vertical thumb grasping motion mode matched with position information of the thumb transmitted from the thumb sensor in the state in which the grasping motion mode is enabled.

The grasping motion execution unit 430 derives a control signal matched with a first main grasping motion detail motion mode and a first subsidiary grasping motion detail motion mode, which are preset, according to an enabling signal transmitted from the first or second electromyography sensor in the state in which the detail motion mode selected by the thumb sensing unit is enabled, and transmits the control signal to the driving unit.

As described above, the grasping motion controller 400 is also configured to store control signals pre-matched with driving signals for unbending or bending fingers according to the first or second enabling signals in each detail motion mode, in the same manner as in the hand mode controller 300, whereby it is possible for the user to perform both the hand motion and the grasping motion using the same enabling signal transmitted from the first or second electromyography sensor.

To this end, the grasping motion setting unit 410 is configured to generate and store a control signal in which each enabling signal is matched with a driving signal for bending or unbending the joints of the fingers in order to show a vertical thumb first main grasping motion to be performed in a first enabling signal state in which a value of HIGH is input from the first electromyography sensor and a value of LOW is input from the second electromyography sensor in the vertical thumb grasping motion mode in which the thumb is located at the vertical position and a vertical thumb first subsidiary grasping motion expressing the state in which a value of HIGH is input from the second electromyography sensor for a sufficient time and a value of LOW is input from the first electromyography sensor in a vertical thumb first main grasping motion detail motion mode. In addition, extension from the vertical thumb first main grasping motion detail motion mode or the vertical thumb first subsidiary grasping motion detail motion mode to a vertical thumb second main grasping motion detail motion mode or a vertical thumb second subsidiary grasping motion detail motion mode expressing a first enabling signal state is possible, as needed.

That is, the grasping motion setting unit 410 is configured to generate and store a first enabling signal (close) in which a value of HIGH is input from the first electromyography sensor and a value of LOW is input from the second electromyography sensor, a second enabling signal (open) in which a value of LOW is input from the first electromyography sensor and a value of HIGH is input from the second electromyography sensor, and a control signal matched with each enabling signal such that switching between the vertical thumb main grasping motion mode and the vertical thumb subsidiary grasping motion mode is performed or at least one subsequent motion mode connected to the vertical thumb main grasping motion mode and at least one second subsequent motion mode connected to the vertical thumb subsidiary grasping motion mode are performed depending on the number of generation times of each signal in the vertical thumb grasping motion mode in which the thumb is located at the vertical position.

Also, even in the horizontal thumb grasping motion mode in which the thumb is located at the horizontal position, the grasping motion setting unit 410 is configured to generate and store a control signal in which each enabling signal is matched with a driving signal for bending or unbending the joints of the fingers in order to show a horizontal thumb first main grasping motion to be performed in the first enabling signal state and a vertical thumb first subsidiary grasping motion expressing the state in which a value of HIGH is input from the second electromyography sensor for a sufficient time and a value of LOW is input from the first electromyography sensor in the horizontal thumb first main grasping motion detail motion mode. In addition, extension from the horizontal thumb first main grasping motion detail motion mode or the horizontal thumb first subsidiary grasping motion detail motion mode to a horizontal thumb second main grasping motion detail motion mode or a horizontal thumb second subsidiary grasping motion detail motion mode expressing a first enabling signal state is possible, as needed.

That is, the grasping motion setting unit 410 is configured to generate and store a first enabling signal (close) in which a value of HIGH is input from the first electromyography sensor and a value of LOW is input from the second electromyography sensor, a second enabling signal (open) in which a value of LOW is input from the first electromyography sensor and a value of HIGH is input from the second electromyography sensor, and a control signal matched with each enabling signal such that switching between the horizontal thumb main grasping motion mode and the horizontal thumb subsidiary grasping motion mode is performed or at least one subsequent motion mode connected to the horizontal thumb main grasping motion mode and at least one subsequent motion mode connected to the horizontal thumb subsidiary grasping motion mode are performed depending on the number of generation times of each signal in the horizontal thumb grasping motion mode in which the thumb is located at the horizontal position.

In this embodiment, as shown in FIG. 2, in the horizontal thumb grasping motion mode in which the thumb is located at the horizontal position, a grip for covering an object having a round outer surface, such as a cylinder or a rod, which is a horizontal thumb first main grasping motion detail motion mode, (expressed as a "cylinder" grip in FIG. 2) and a grip for stably holding one surface of a thin and wide object, such as a card, which is a horizontal thumb first subsidiary grasping motion detail motion mode, (expressed as a "lateral" grip in FIG. 2) are set. Also, in the vertical thumb motion mode in which the thumb is located at the vertical position, a grip for widely covering the outer circumferential surface of a large object, which is a vertical thumb first main grasping motion detail motion mode, (expressed as a "power" grip in FIG. 2) and a grip for lightly holding a small object using some fingers, which is a vertical thumb first subsidiary grasping motion detail motion mode, (expressed as a "tip (precision)" grip in FIG. 2) are set. However, the type of the grip set in each detail motion mode is not limited thereto and may be variously set depending on the form of the grip mainly used by the user.

In addition, the thumb sensing unit 420 is configured to enable the horizontal thumb grasping motion mode and the vertical thumb grasping motion mode matched with the horizontal position or the vertical position based on the position information of the thumb transmitted from the thumb sensor in the state in which the grasping motion mode is enabled, in the same manner as in the grasping motion controller 400.

In addition, the grasping motion execution unit 430 is configured to derive a control signal matched with an enabling signal transmitted from the first or second electromyography sensor in the state in which a main grasping motion detail motion mode and a subsidiary grasping motion detail motion mode set in each thumb position motion mode selected based on the position of the thumb are enabled and to transmit the control signal to the driving unit of the myoelectric hand.

As shown in FIG. 2, therefore, when the first enabling signal (close signal), in which a value of HIGH is input from only the first electromyography sensor, is applied in the horizontal thumb motion mode in which the thumb is located at the horizontal position, distal ends of the fingers except for the thumb are curled to cover an object having a round outer circumferential surface, such as a rod or a cylinder, in order to form the "cylinder" grip, which is a horizontal thumb first main grasping motion detail motion mode matched with the first enabling signal. Afterwards, when the second enabling signal (open signal), in which a value of HIGH is input from only the first electromyography sensor, is applied, the fingers are unbent again and are then restored to the state before grasping is performed.

Also, in order to show a horizontal thumb first subsidiary grasping motion detail motion mode expressing the state in which a value of HIGH is input from the second electromyography sensor for a sufficient time and a value of LOW is input from the first electromyography sensor in the horizontal thumb first main grasping motion detail motion mode in which the thumb is located at the horizontal position, the grasping motion execution unit performs switching to the horizontal thumb first subsidiary grasping motion detail motion mode in order to form the "lateral" grip so as to stably grasp a wide surface of a thin object, such as a card. In the horizontal thumb first subsidiary grasping motion mode, therefore, when the first enabling signal (close signal) is generated, the fingers of the myoelectric hand are driven to form the "lateral" grip, as shown in FIG. 2.

Afterwards, when a signal (open signal in FIG. 2) opposite the first enabling signal (close signal) is input from the first or second electromyography sensor, the fingers of the myoelectric hand are restored to the state before the grasping motion is performed. At this time, when an opposite signal (open signal in FIG. 2) is input for a sufficient time, a new detail motion mode is ready through detail motion mode switching. That is, the main motion detail motion mode is switched to the subsidiary motion detail motion mode, and the subsidiary motion detail motion mode is switched to the main motion detail motion mode.

In addition, when the first enabling signal (close signal), in which a value of HIGH is input from only the first electromyography sensor, is applied in the vertical thumb grasping motion mode in which the thumb is located at the vertical position, the grasping motion execution unit is converted into a state in which distal ends of all of the thumb and the fingers are curled to more strongly cover an object in order to form the "power" grip, which is a vertical thumb first main grasping motion. Afterwards, when the second enabling signal (close signal), in which a value of HIGH is input from only the second electromyography sensor, is applied, the thumb and the fingers are restored to the state before grasping is performed.

In addition, when a value of HIGH is input from the second electromyography sensor for a sufficient time and a value of LOW is input from the first electromyography sensor in the vertical thumb first main grasping motion detail motion mode, the grasping motion execution unit performs switching to the vertical thumb first subsidiary grasping motion detail motion mode in order to form the "tip (precision)" grip so as to lightly grasp a small object using only the thumb and the index finger. In the vertical thumb first subsidiary grasping motion mode, therefore, when the first enabling signal (close signal) is generated, the fingers of the myoelectric hand are driven to form the "tip (precision)" grip, as shown in FIG. 2.

Afterwards, when a signal (open signal in FIG. 2) opposite the first enabling signal (close signal) is input from the first or second electromyography sensor, the fingers of the myoelectric hand are restored to the state before the grasping motion is performed. At this time, when an opposite signal (open signal in FIG. 2) is input for a sufficient time, a new detail motion mode is ready through detail motion mode switching. That is, the main motion detail motion mode is switched to the subsidiary motion detail motion mode, and the subsidiary motion detail motion mode is switched to the main motion detail motion mode.

In the motion-mode- and thumb-position-based motion control system of the myoelectric hand according to the present invention, as described above, a grasping motion for picking up an object or a hand motion used to express user emotion or intention is set as a separate mode, and data set for a motion in any one mode are configured not to affect a motion in another mode, whereby it is possible to perform a hand motion as well as a grasping motion driven in various detail motion modes using only an enabling signal constituted by electromyography signals transmitted from the two electromyography sensors without assistance of an additional device, such as another application (APP) or dongle, and therefore it is possible to conveniently expand the range within which the myoelectric hand is used.

Also, in the present invention, the hand motion mode, which is implemented by a single motion, and the grasping motion, which is performed by repetitive signal generation, are clearly distinguished from each other, whereby the user may easily learn various motions, and therefore it is possible to minimize inconvenience in learning a complicated and difficult manipulation method.

Next, a motion-mode- and thumb-position-based motion control method of the myoelectric hand according to the present invention constructed as described above will be described.

Figure 3:
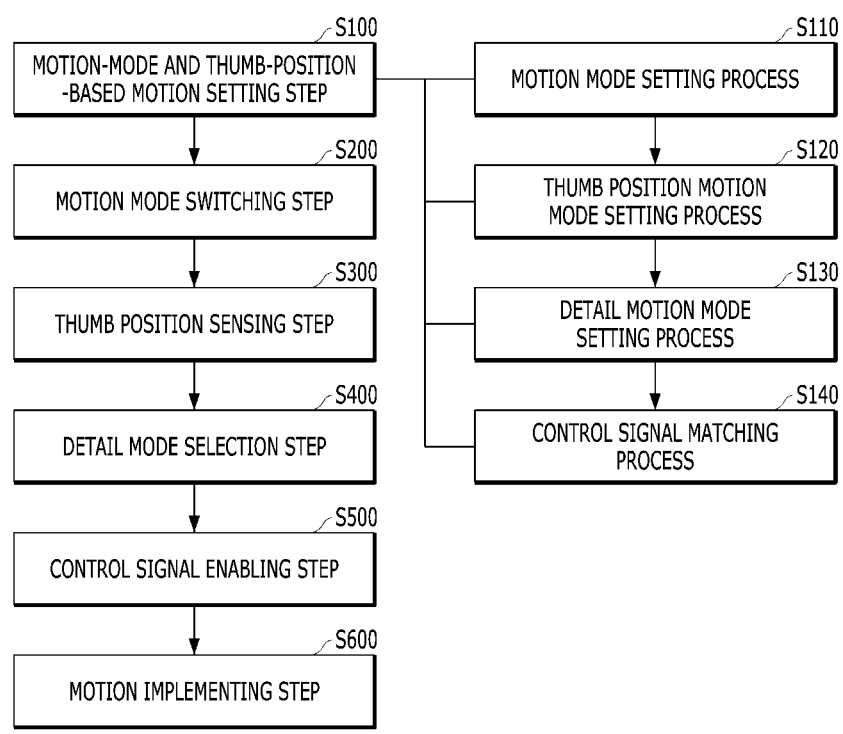
FIG. 3 is a flowchart of a motion-mode- and thumb-position-based motion control method of a myoelectric hand showing various hand motions and grasping motions in accordance with the present invention.
Figure 4:
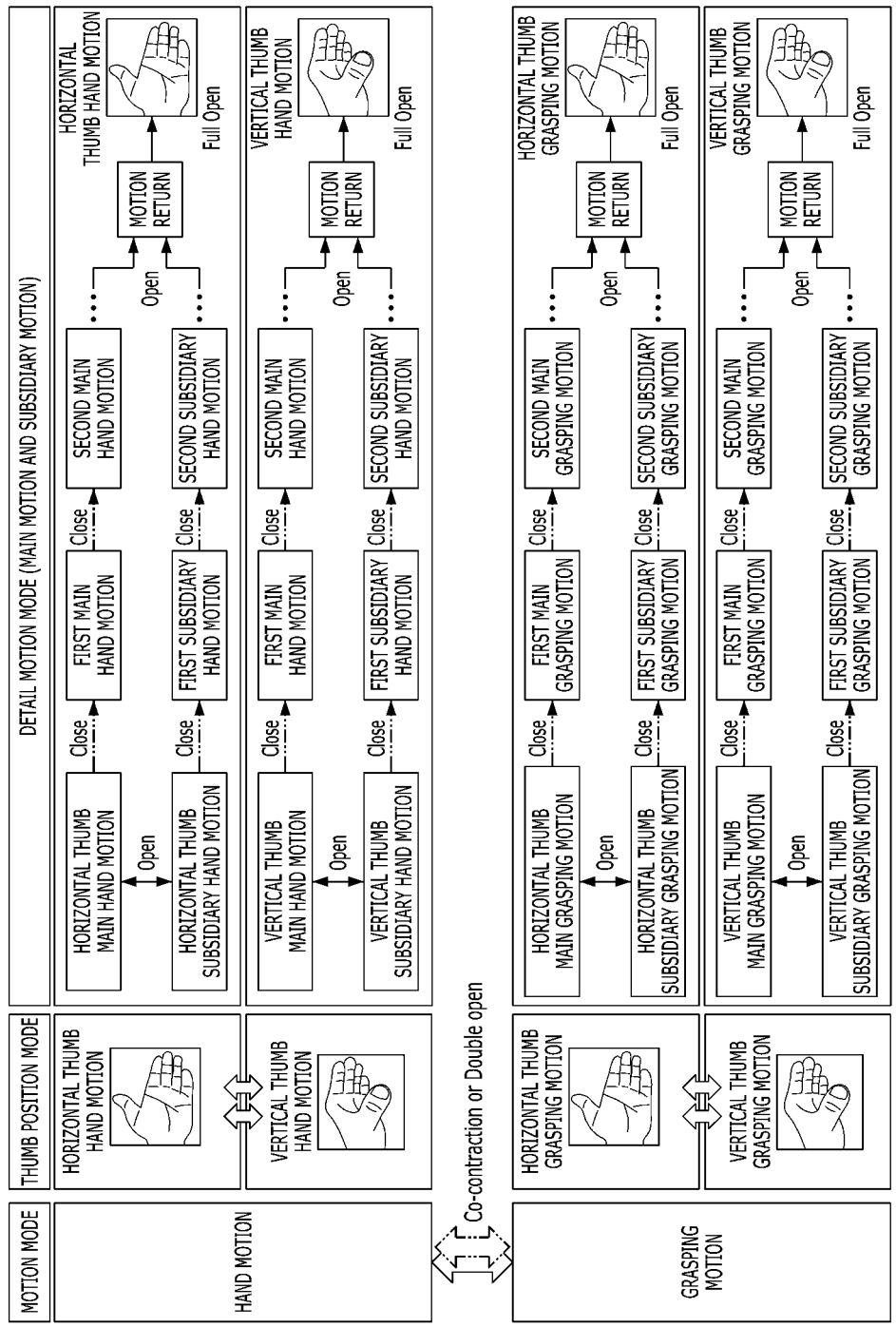
FIG. 4 is a view showing main/subsidiary hand motions and main/subsidiary grasping motions based on the position of a thumb and the state of an electromyographic signal in accordance with the present invention.

FIG. 3 is a flowchart of a motion-mode- and thumb-position-based motion control method of a myoelectric hand showing various hand motions and grasping motions in accordance with the present invention, and FIG. 4 is a view showing main/subsidiary hand motions and main/subsidiary grasping motions based on the position of a thumb and the state of an electromyographic signal in accordance with the present invention.

Referring to FIG. 3, the motion-mode- and thumb-position-based motion control method of the myoelectric hand according to the present invention includes a motion-mode- and thumb-position-based motion setting step (S100) of classifying motion modes to be implemented by the myoelectric hand into a hand motion mode and a grasping motion mode, setting, for each of horizontal thumb and vertical thumb motion modes depending on the position of the thumb, a control signal for forming the shape of fingers or a grip to be implemented in each motion mode, and storing main motion and subsidiary motion detail motion modes for each mode, a motion mode switching step (S200) of, when a predetermined combination signal (co-contraction or double open) is input from two electromyography sensors provided at the myoelectric hand, switching a motion mode to be enabled between the hand motion mode and the grasping motion mode, a thumb position sensing step (S300) of acquiring the position of a thumb manipulated by a user based on position information transmitted from a thumb sensor to determine whether the motion mode is a horizontal thumb motion mode or a vertical thumb motion mode, a detail motion mode selection step (S400) of determining whether the position of the thumb is a horizontal position or a vertical position and enabling a main motion detail motion mode and a subsidiary motion detail motion mode set in each of the horizontal thumb motion mode and the vertical thumb motion mode, a control signal enabling step (S500) of deriving a control signal for performing a hand motion or a grasping motion set in each detail motion mode according to electromyography signals transmitted from the two electromyography sensors, and a motion implementing step (S600) of, upon receiving the enabled control signal, the myoelectric hand performing the set hand motion or grasping motion while bending or unbending the joints of the fingers.

The motion-mode- and thumb-position-based motion setting step (S100) includes a motion mode setting process (S110) of setting motions to be implemented by the myoelectric hand so as to be classified into a hand motion mode for showing the shapes of fingers used for emotion expression or intention expression and a grasping motion mode for forming various grips to hold an object, a horizontal thumb and vertical thumb motion mode setting process (S120) of storing the shapes of fingers or grips to be implemented in each motion mode in a state of being matched with the vertical position and the horizontal position based on position information of the thumb, a main motion and subsidiary motion detail motion mode setting process (S130) of storing main motion and subsidiary motion detail motion modes in a state of being matched with the vertical position and the horizontal position of the thumb, and a control signal matching process (S140) of storing a control signal for driving the myoelectric hand such that the joints of the fingers are bent or unbent in order to implement the shapes of fingers and the grips matched with each detail motion mode in a state of being matched with each shape of fingers and each grip.

In the motion-mode- and thumb-position-based motion setting step (S100), as described above, both the hand motion and the grasping motion are implemented according to restrictive electromyography signals transmitted from the two electromyography sensors, and a horizontal thumb position mode and a vertical thumb position mode are set based on the position of the thumb that can be changed by the user manually and automatically rotating the thumb in order to diversify hand motions and grips that can be implemented.

In the hand motion mode, therefore, it is possible to perform a plurality of hand motions through a thumb position hand motion mode changed depending on the position of the thumb even though the electromyography signals transmitted from the two electromyography sensors are the same. In the same manner, even in the grasping motion mode, a grasping grip different for each thumb position grasping motion mode changed depending on the position of the thumb is implemented using the same electromyography signals.

In the motion mode switching step (S200), whenever a simultaneous enabling signal (co-contraction signal) constituted by electromyography signals each having a value of HIGH is input from the two electromyography sensors provided at the myoelectric hand or whenever a double open signal or an enabling signal set by a combination of two signals is input, a motion mode to be enabled is switched between the hand motion mode and the grasping motion mode.

Consequently, it is possible for the user to enable a predetermined combination (co-contraction or double open) of signals from the two electromyography sensors in the same manner as a method learned for an ordinary grasping motion without manipulation of an application (APP) or dongle installed in a separate smartphone, whereby it is possible to switch between the hand motion mode and the grasping motion mode.

In the thumb position sensing step (S300), the position of the thumb manually/automatically rotated by the user is acquired based on the position information transmitted from the thumb sensor, and a determination is made as to whether the thumb is at the vertical position, at which the thumb is perpendicular to the fingers, or the thumb is rotated and is at the horizontal position, at which the thumb is parallel to the fingers.

In the detail motion mode selection step (S400), the main motion detail motion mode and the subsidiary motion detail motion mode matched with the horizontal thumb motion mode or the vertical thumb motion mode based on the position of the thumb determined in the thumb position sensing step are selected as detail motion modes of the hand motion mode or the grasping motion mode to be enabled according to the electromyography signal transmitted from the electromyography sensor.

Consequently, whenever the position of the thumb is changed within the motion mode selected by the user in the motion mode switching step (S200), a detail motion mode showing the hand motion to be enabled according to the electromyography signal or showing a grip for grasping an object is changed, whereby it is possible to maintain diversity in hand motions and grasping grips that can be performed using the myoelectric hand while using a predetermined combination (co-contraction or double open) of signals from the two electromyography sensors in order to switch the motion mode and the thumb position.

In the control signal enabling step (S500), a control signal set to form the shape of fingers and the grasping grip set in each detail motion mode selected in the detail motion mode selection step according to the electromyography signals transmitted from the two electromyography sensors is derived.

At this time, driving signals for driving the driving unit provided at the myoelectric hand in order to bend or unbend the joints of several fingers of the myoelectric hand so as to implement the shape of fingers and the grip to be formed are matched with the control signal. It is possible to enable driving signals for forming the shape of fingers and the grasping grip merely by deriving a control signal based on the two electromyography signals input through the two electromyography sensors.

In the motion implementing step (S600), a driving signal matched with the control signal enabled in the control signal enabling step is transmitted to the driving unit of the myoelectric hand such that a preset shape of the fingers or a preset grasping grip is formed.

As described above, it is possible to perform an ordinary grasping motion using the same electromyography signals transmitted from the two electromyography sensors and to perform a hand motion for showing various intention expressions or emotion expressions without a separate additional device, whereby it is possible to improve daily convenience and quality of life of the user who wears the myoelectric hand.

As is apparent from the above description, the present invention has effects in that it is possible to perform a hand motion indicating emotion or intention expression as well as a grasping motion for holding an object according to restrictive electromyography signals transmitted from two electromyography sensors provided at a myoelectric hand and in that it is possible to classify hand motions and grips into main motions and subsidiary motions depending on the position of a thumb, whereby it is possible to diversify the hand motions and the grips.

In addition, the present invention has an effect in that it is possible to grasp an object and perform various hand motions without provision of an additional device, such as an application (APP) or dongle, whereby it is possible to easily expand the range within which the myoelectric hand is used.

In addition, implementation is possible through a simple motion signal, whereby it is possible to improve user convenience in use.

Although all components constituting an embodiment of the present invention were described as being coupled as a single body or being operated in a state of being coupled as a single body above, the present invention is not limited to such an embodiment. That is, all of the components may be optionally coupled as one or more bodies so as to be operated within the scope of object of the present invention. In addition, the terms "include," "comprise" and "have" mean that elements can be inherent unless otherwise stated. Therefore, the terms should be interpreted not to exclude other elements but to further include such other elements. All terms including technical or scientific terms have the same meanings as generally understood by a person having ordinary skill in the art to which the present invention pertains unless mentioned otherwise. Generally used terms, such as terms defined in a dictionary, should be interpreted to coincide with meanings of the related art from the context. Unless obviously defined in the present invention, such terms are not interpreted as having ideal or excessively formal meanings.

The above description merely illustrates the technical concept of the present invention, and it will be apparent to those skilled in the art that various modifications and alterations are possible without departing from intrinsic characteristics of the present invention. Therefore, the embodiments of the present invention do not define but describe the technical concept of the present invention, and the scope of the technical concept of the present invention is not limited by the embodiments. The scope of protection of the present invention should be determined by the appended claims, and all changes falling within the meaning and equivalency range of the appended claims are intended to be embraced therein.

What is claimed is:

1. A myoelectric hand control system comprising:
a motion mode switching unit configured to enable a hand motion controller or a grasping motion controller;
a thumb sensor configured to determine whether a thumb of the myoelectric hand is in a horizontal position or a vertical position;
the hand motion controller configured to, based on the motion mode switching unit enabling the hand motion controller:
receive an electromyography signal from a first electromyography sensor attached to a human body, and
transmit a control signal to a driving unit of the myoelectric hand to drive the myoelectric hand to cause the myoelectric hand to perform a hand gesture based on the determined position of the thumb; and
the grasping motion controller configured to, based on the motion mode switching unit enabling the grasping motion controller:
receive the electromyography signal from the first electromyography sensor attached to the human body, and
transmit the control signal to the driving unit of the myoelectric hand to drive the myoelectric hand to cause the myoelectric hand to perform a hand motion relative to an object based on the determined position of the thumb, wherein:
the motion mode switching unit is configured to switch between enabling the hand motion controller and the grasping motion controller based on a combined signal from the first electromyography sensor and a second electromyography sensor; the combined signal comprises a simultaneous enabling signal or an open signal for a predetermined time, wherein:
the simultaneous enabling signal corresponds to values of HIGH being applied from both the first electromyography sensor and the second electromyography sensor; and
the open signal corresponds to a value of LOW being applied from the first electromyography sensor and a value of HIGH being applied twice from the second electromyography sensor;
the hand motion controller comprises:
a hand motion setting unit configured to generate a plurality of enabling signals configured to cause the driving unit to unbend or bend fingers of the myoelectric hand according to the electromyography signal from the first electromyography sensor or the second electromyography sensor;
a thumb sensing unit configured to enable a horizontal thumb hand motion mode or a vertical thumb hand motion mode based on the determined position of the thumb; and
a hand motion execution unit configured to:
generate the control signal based on the enabled mode and the plurality of enabling signals; and
transmit the control signal to the driving unit,
wherein the hand motion setting unit is configured to generate and store a first enabling signal, a second enabling signal, or a signal matched with each enabling signal of the plurality of enabling signals, wherein:
the first enabling signal corresponds to a value of HIGH being input from the first electromyography sensor and a value of LOW being input from the second electromyography sensor;
the second enabling signal corresponds to a value of LOW being input from the first electromyography sensor and a value of HIGH being input from the second electromyography sensor; and
the hand motion setting unit is configured to switch between a horizontal thumb main hand motion mode and a horizontal thumb subsidiary hand motion mode or at least one subsequent motion mode connected to the horizontal thumb main hand motion mode, and at least one subsequent motion mode connected to the horizontal thumb subsidiary hand motion mode based on a number of generation times of each signal in the horizontal thumb hand motion, wherein the hand motion setting unit is configured to:

switch between the horizontal thumb main hand motion mode and the horizontal thumb subsidiary hand motion mode when the second enabling signal is received;

set a horizontal thumb first main hand motion detail motion mode to cause the myoelectric hand to perform a hand gesture indicating scissors of rock paper scissors when the first enabling signal is input in the horizontal thumb main hand motion mode, wherein the thumb is in the horizontal position for the hand gesture indicating scissors;

set a horizontal thumb second main hand motion detail motion mode to cause the myoelectric hand to perform a hand gesture indicating rock of the rock paper scissors when the first enabling signal is input again in the horizontal thumb first main hand motion detail motion mode, wherein the thumb is in the horizontal position and outside of the fingers of the myoelectric hand for the hand gesture indicating rock;

set returning to the horizontal thumb hand motion mode when the second enabling signal is input in the horizontal thumb second main hand motion detail motion mode;

set a vertical thumb first subsidiary hand motion detail motion mode to cause the myoelectric hand to perform a hand gesture indicating thumbs-up when the first enabling signal is input in the horizontal thumb subsidiary hand motion mode; and set returning to the horizontal thumb hand motion mode when the second enabling signal is input in the vertical thumb first subsidiary hand motion detail motion mode.

2. The myoelectric hand control system according to claim 1, wherein the hand motion setting unit is configured to generate and store the first enabling signal, the second enabling signal, or a signal matched with each enabling signal of the plurality of enabling signals, wherein:

the first enabling signal corresponds to a value of HIGH being input from the first electromyography sensor and a value of LOW being input from the second electromyography sensor, the second enabling signal corresponds to a value of LOW being input from the first electromyography sensor and a value of HIGH being input from the second electromyography sensor, and the hand motion setting unit is configured to switch between a vertical thumb main hand motion mode and a vertical thumb subsidiary hand motion mode or at least one first main hand motion mode connected to the vertical thumb main hand motion mode and at least one second subsidiary hand motion mode connected to the vertical thumb subsidiary hand motion mode based on a number of generation times of each signal in the vertical thumb hand motion mode.

3. The myoelectric hand control system according to claim 2, wherein the hand motion setting unit is configured:

to set switching between the vertical thumb main hand motion mode and the vertical thumb subsidiary hand motion mode whenever the second enabling signal is input in the vertical thumb hand motion mode;

to set a vertical thumb first subsidiary hand motion detail motion mode so as to perform an OK hand motion when the first enabling signal is input in the vertical thumb subsidiary hand motion mode, wherein the thumb is in the vertical position and in contact with at least one of the fingers of the myoelectric hand for the OK hand motion; and to set returning to the vertical thumb hand motion mode when the second enabling signal is input in the vertical thumb first subsidiary hand motion detail motion mode.

4. The myoelectric hand control system according to claim 1, wherein the grasping motion controller comprises:

a grasping motion setting unit configured to generate the plurality of enabling signals configured to cause the driving unit to grasp an object while unbending or bending fingers the electromyography signal from the first electromyography sensor or the second electromyography sensor;

a thumb sensing unit configured to enable a horizontal thumb grasping motion mode or a vertical thumb grasping motion mode based on the determined position of the thumb; and a grasping motion execution unit configured to:
generate the control signal based on the enabled mode and the plurality of enabling signals; and
transmit the control signal to the driving unit.

5. The myoelectric hand control system according to claim 4, wherein the grasping motion setting unit is configured to generate and store the first enabling signal, the second enabling signal, or a signal matched with each enabling signal of the plurality of enabling signals, wherein:

the first enabling signal corresponds to a value of HIGH being input from the first electromyography sensor and a value of LOW being input from the second electromyography sensor, the second enabling signal corresponds to a value of LOW being input from the first electromyography sensor and a value of HIGH being input from the second electromyography sensor, and the hand motion setting unit is configured to switch between a horizontal thumb main grasping motion mode and a horizontal thumb subsidiary grasping motion mode or at least one subsequent motion mode connected to the horizontal thumb main grasping motion mode and at least one subsequent motion mode connected to the horizontal thumb subsidiary grasping motion mode based on a number of generation times of each signal in the horizontal thumb grasping motion mode.

6. The myoelectric hand control system according to claim 5, wherein the grasping motion setting unit is configured:

to set switching between the horizontal thumb main grasping motion mode and the horizontal thumb subsidiary grasping motion mode whenever the second enabling signal is input in the horizontal thumb grasping motion mode;

to set a horizontal thumb first main grasping motion detail motion mode so as to perform a cylinder grip grasping motion when the first enabling signal is input in the horizontal thumb main grasping motion mode;

to set returning to the horizontal thumb grasping motion mode when the second enabling signal is input in the horizontal thumb first main grasping motion detail motion mode;

to set a horizontal thumb first subsidiary grasping motion detail motion mode so as to perform a lateral grip grasping motion when the first enabling signal is input in the horizontal thumb subsidiary grasping motion mode; and to set returning to the horizontal thumb grasping motion mode when the second enabling signal is input in the horizontal thumb first subsidiary grasping motion detail motion mode.

7. The myoelectric hand control system according to claim 4, wherein the grasping motion setting unit is configured to generate and store the first enabling signal, the second enabling signal, or a signal matched with each enabling signal, wherein:
- the first enabling signal corresponds to a value of HIGH being input from the first electromyography sensor and a value of LOW being input from the second electromyography sensor;
- the second enabling signal corresponds to a value of LOW being input from the first electromyography sensor and a value of HIGH being input from the second electromyography sensor; and
- the hand motion setting unit is configured to switch between a vertical thumb main grasping motion mode and a vertical thumb subsidiary grasping motion mode or at least one subsequent motion mode connected to the vertical thumb main grasping motion mode, and at least one subsequent motion mode connected to the vertical thumb subsidiary grasping motion mode based on a number of generation times of each signal in the vertical thumb grasping motion mode.

8. The myoelectric hand control system according to claim 7, wherein the grasping motion setting unit is configured to:
- switch between the vertical thumb main grasping motion mode and the vertical thumb subsidiary grasping motion mode when the second enabling signal is received;
- set a vertical thumb first main grasping motion detail motion mode to cause the myoelectric hand to perform a power grip grasping motion when the first enabling signal is input in the vertical thumb main grasping motion mode;
- set returning to the vertical thumb grasping motion mode when the second enabling signal is input in the vertical thumb first main grasping motion detail motion mode;
- set a vertical thumb first subsidiary grasping motion detail motion mode to cause the myoelectric hand to perform a tip precision grip grasping motion when the first enabling signal is input in the vertical thumb subsidiary grasping motion mode; and
- set returning to the vertical thumb grasping motion mode when the second enabling signal is input in the vertical thumb first subsidiary grasping motion detail motion mode.

* * * * *